(12) United States Patent
Sgroi, Jr.

(10) Patent No.: US 11,065,005 B2
(45) Date of Patent: Jul. 20, 2021

(54) RELOAD ASSEMBLY FOR A CIRCULAR STAPLING DEVICE

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 7 days.

(21) Appl. No.: 16/598,324

(22) Filed: Oct. 10, 2019

(65) Prior Publication Data

US 2020/0138441 A1 May 7, 2020

Related U.S. Application Data

(60) Provisional application No. 62/756,802, filed on Nov. 7, 2018.

(51) Int. Cl.
*A61B 17/115* (2006.01)
*A61B 17/068* (2006.01)
(Continued)

(52) U.S. Cl.
CPC ........ *A61B 17/1155* (2013.01); *A61B 17/068* (2013.01); *A61B 2017/0053* (2013.01);
(Continued)

(58) Field of Classification Search
CPC .............. A61B 17/1155; A61B 17/068; A61B 2017/0053; A61B 2017/0688; A61B 2017/07257; A61B 2217/002; A61B 2017/07285; A61B 90/98; A61B 2017/00473; A61B 34/30; A61B 2090/034; A61B 17/105; A61B 17/07207; A61B 90/90; A61B 2017/07278; A61B 2017/00398; A61B 2017/00477; A61B 2017/00951; A61B 2017/07271; A61B 2017/2927; A61B 2090/038;
(Continued)

(56) References Cited

U.S. PATENT DOCUMENTS 3,193,165 A 7/1965 Akhalaya et al.
3,388,847 A 6/1968 Kasulin et al.
(Continued)

FOREIGN PATENT DOCUMENTS

CA 908529 A 8/1972
CA 2805365 A1 8/2013
(Continued)

OTHER PUBLICATIONS

European Search Report dated Mar. 24, 2020, issued in EP Appln. No. 19207357, 8 pages.

*Primary Examiner* — Robert F Long

(57) ABSTRACT

A reload assembly includes a shell housing, a knife carrier, and at least one engagement member. The shell housing includes an inner housing portion and an outer housing portion that is spaced from the inner housing portion to define an annular cavity. A catch is supported within the annular cavity. The knife carrier defines a longitudinal axis and supports a knife. The knife carrier also supports a resilient locking member that is positioned to engage the catch when the knife carrier is in its retracted position after the reload assembly has been fired to retain the knife carrier in the retracted position.

24 Claims, 14 Drawing Sheets

(51) Int. Cl.
*A61B 17/00* (2006.01)
*A61B 17/072* (2006.01)

(52) U.S. Cl.
CPC ............... *A61B 2017/0688* (2013.01); *A61B 2017/07257* (2013.01); *A61B 2217/002* (2013.01)

(58) Field of Classification Search
CPC .. A61B 2090/0808; A61B 2017/00982; A61B 2017/00017; A61B 2562/0261; A61B 2017/00526; A61B 90/03; A61B 50/13; A61B 50/33; A61B 90/92; A61B 2090/0803; A61B 2090/031; A61B 2018/0063; A61B 2018/00988; A61B 18/1445; A61B 2018/1455; A61B 2017/00725; A61B 2017/0785; A61B 17/29; A61B 2017/00836; A61B 2017/00734; A61B 2017/00039; A61B 2017/00862; A61B 17/07292
USPC ................................ 227/175.1–182.1
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,326,013 A * | 7/1994 | Green ............... A61B 17/07207 227/176.1 |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,529,235 A * | 6/1996 | Boiarski ............... A61B 90/98 227/175.1 |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |

(56) References Cited

U.S. PATENT DOCUMENTS

| | | |
|---|---|---|
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |

(56) References Cited

U.S. PATENT DOCUMENTS

| | | |
|---|---|---|
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,504,470 B2 * | 11/2016 | Milliman .......... A61B 17/07292 |
| 9,883,860 B2 * | 2/2018 | Leimbach .............. A61B 34/76 |
| 10,321,911 B2 * | 6/2019 | Milliman .......... A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |

(56) References Cited

U.S. PATENT DOCUMENTS

| | | |
|---|---|---|
| 2010/0108741 A1 | 5/2010 | Hessler et al. |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0292368 A1 | 11/2012 | Nalagatla et al. |
| 2012/0292371 A1* | 11/2012 | Nalagatla .......... A61B 17/1155 227/179.1 |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0239046 A1* | 8/2014 | Milliman .......... A61B 17/07292 227/180.1 |
| 2015/0014393 A1* | 1/2015 | Milliman ........... A61B 17/1155 227/180.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0249928 A1* | 9/2016 | Cappola .......... A61B 17/07207 227/176.1 |
| 2016/0302792 A1 | 10/2016 | Motai |
| 2018/0125486 A1 | 5/2018 | Guerrera |
| 2018/0271524 A1* | 9/2018 | Williams .............. A61B 17/072 |
| 2019/0328395 A1* | 10/2019 | Milliman ............ A61B 17/1155 |
| 2020/0163675 A1* | 5/2020 | Sgroi, Jr. .......... A61B 17/3209 |
| 2020/0276693 A1* | 9/2020 | Sgroi, Jr. ............... B25C 5/1617 |
| 2020/0330099 A1* | 10/2020 | Williams ............ A61B 17/1155 |
| 2021/0016426 A1* | 1/2021 | Sgroi, Jr. ............ A61B 17/1155 |
| 2021/0022732 A1* | 1/2021 | Valentine ................ A61B 90/03 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2233926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 a1 | 8/2001 |
| WO | 20208107918 A1 | 9/2008 |

* cited by examiner

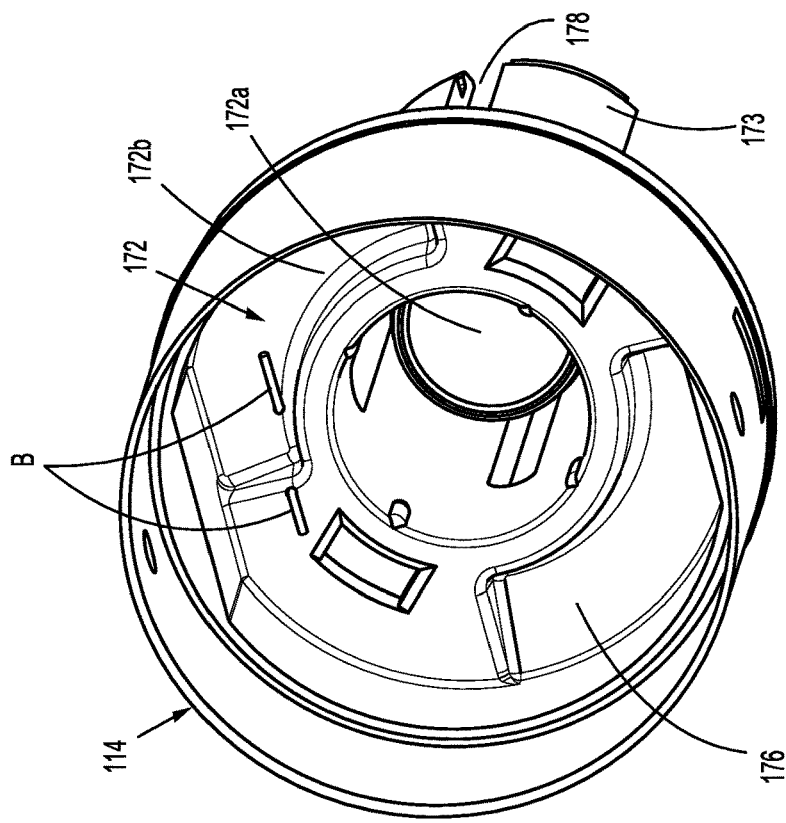
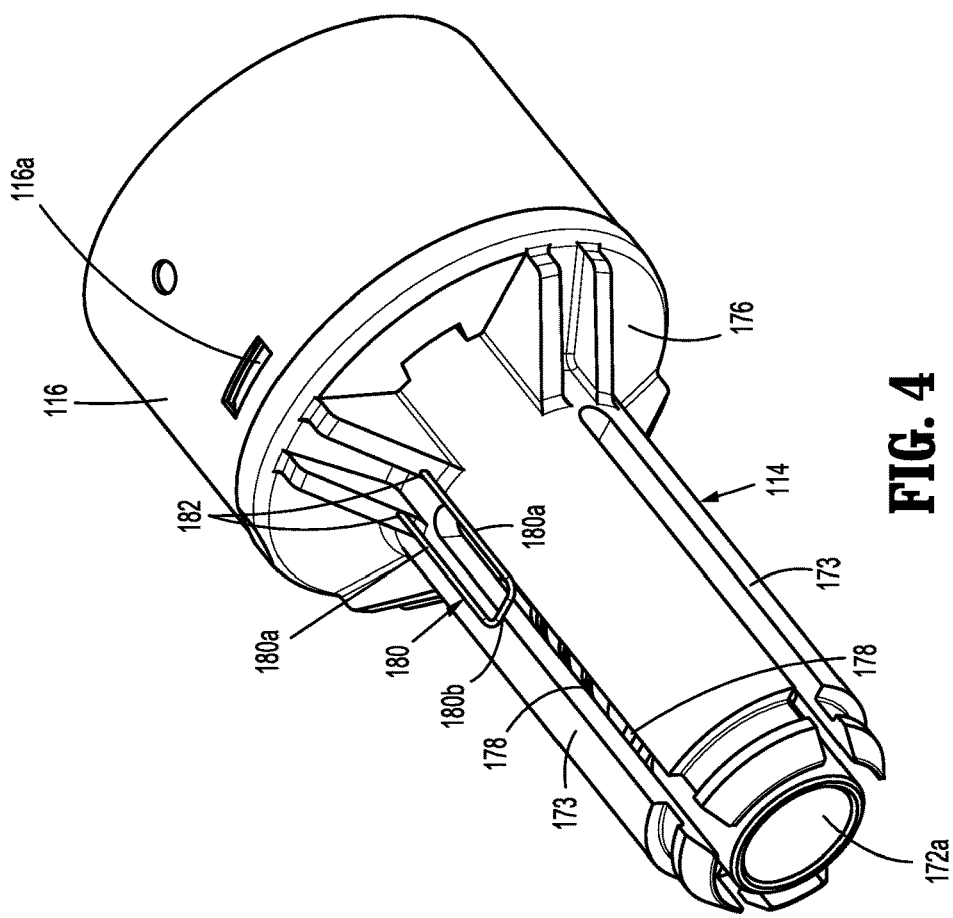
FIG. 5
FIG. 4

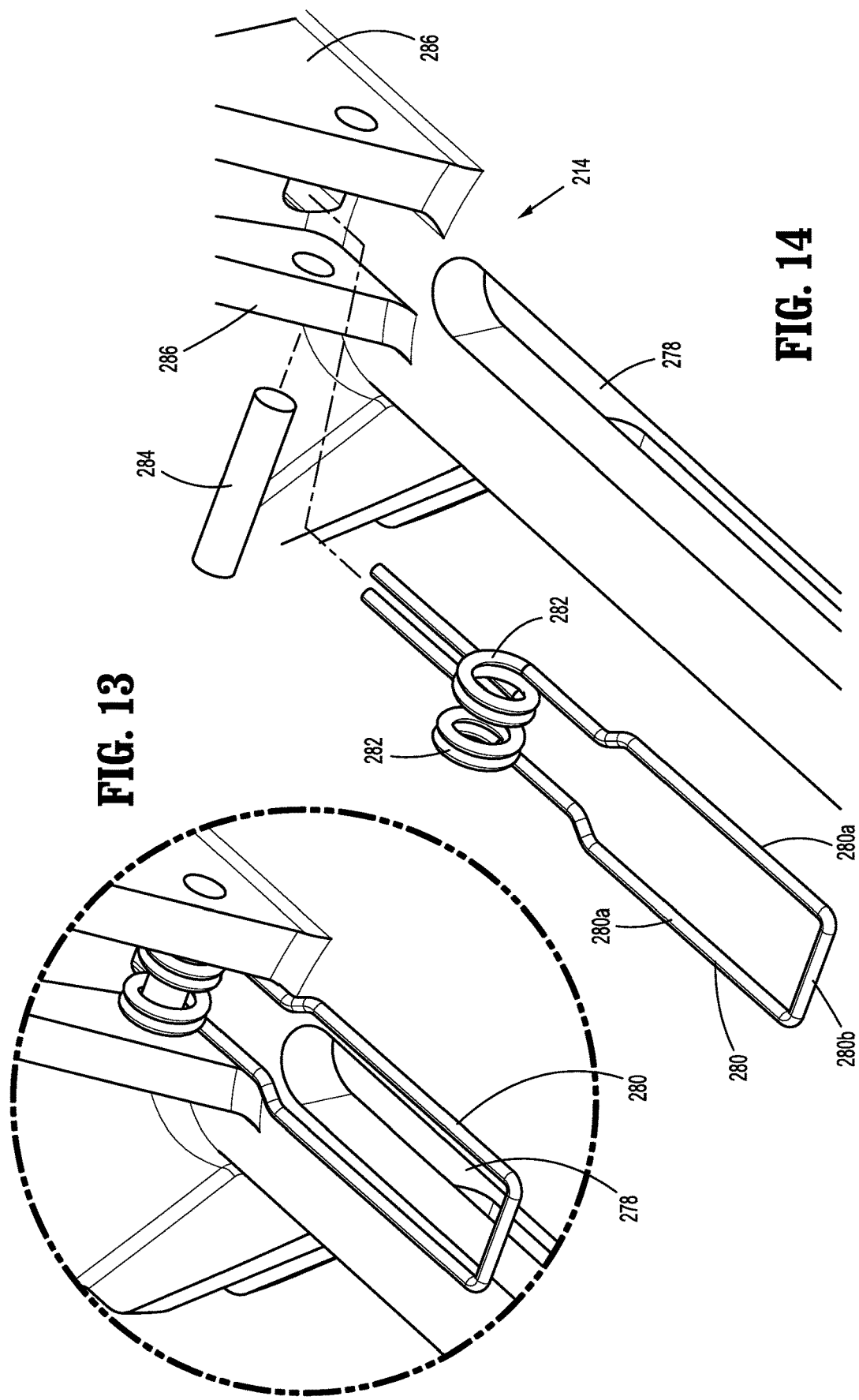

RELOAD ASSEMBLY FOR A CIRCULAR STAPLING DEVICE

CROSS-REFERENCE TO RELATED APPLICATIONS

This application claims the benefit of and priority to U.S. Provisional Patent Application Ser. No. 62/756,802 filed Nov. 7, 2018, the entire disclosure of which is incorporated by reference herein.

BACKGROUND

1. Technical Description

The present disclosure is directed to circular stapling devices and, more particularly, to reload assemblies for circular stapling devices with structure to retain a knife carrier in a retracted position after the stapling device is fired.

2. Background of Related Art

Conventional circular stapling devices include an elongate body and a shell or reload assembly that is supported on a distal portion of the elongate body. The reload assembly includes a shell housing, a staple cartridge supported on the shell housing having a plurality of staples, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core tissue After a stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

In some instances, the tissue donut is compressed within the cavity defined by the knife to such a degree that removal of the tissue donut from within the cavity defined by the knife is difficult. A continuing need exists in the art for a reload assembly that includes improved structure for retaining the knife/knife carrier in a retracted position.

SUMMARY

One aspect of the present disclosure is directed to a reload assembly including a shell housing, a staple cartridge, a pusher, a knife carrier, a catch, and a locking member. The shell housing includes an inner housing portion and an outer housing portion. The inner housing portion is spaced from the outer housing portion to define an annular cavity between the inner and outer housing portions. The staple cartridge is supported on a distal portion of the shell housing and has a plurality of staple pockets, each receiving a staple. The pusher is supported within the annular cavity and is movable between a retracted position and an advanced position to eject the staples from the staple cartridge. The knife carrier includes a body defining a longitudinal axis and supporting a knife. The body of the knife carrier defines a central bore and a longitudinal slot communicating with the central bore. The inner housing portion of the shell housing is positioned within the central bore of the knife carrier such that the knife carrier is movable about the inner housing portion of the shell housing between advanced and retracted positions. The catch is positioned within the annular cavity of the shell housing. The locking member is supported on the knife carrier and is movable from a biased state to an unbiased state, wherein in the unbiased state, the locking member is positioned to engage the catch to retain the knife carrier in the retracted position.

Another aspect of the present disclosure is directed to a circular stapling device including an elongate body, and a reload assembly. The elongate body has a proximal portion and a distal portion. The reload assembly is supported on the distal portion of the elongate body and includes a shell housing, a staple cartridge, a pusher, a knife carrier, a catch, and a locking member. The shell housing includes an inner housing portion and an outer housing portion. The inner housing portion is spaced from the outer housing portion to define an annular cavity between the inner and outer housing portions. The staple cartridge is supported on a distal portion of the shell housing and defines a plurality of staple pockets each receiving a staple. The pusher is supported within the annular cavity and is movable between a retracted position and an advanced position to eject the staples from the staple cartridge. The knife carrier includes a body that defines a longitudinal axis and supports a knife. The body of the knife carrier defines a central bore and a longitudinal slot communicating with the central bore. The inner housing portion of the shell housing is positioned within the central bore of the knife carrier such that the knife carrier moves about the inner housing portion of the shell housing between advanced and retracted positions. The catch is positioned within the annular cavity of the shell housing. The locking member is supported on the knife carrier and is movable from a biased state to an unbiased state, wherein in the unbiased state, the locking member is positioned to engage the catch to retain the knife carrier in the retracted position.

In embodiments, the catch includes a hook-portion that extends into the longitudinal slot.

In some embodiments, the catch includes a cam surface and the locking member is supported on the cam surface in the biased state when the knife carrier is in the retracted position prior to firing of the reload assembly.

In certain embodiments, the locking member includes a U-shaped spring arm having first and second legs and a back span that extends between the first and second legs.

In embodiments, the spring arm is supported on an outer surface of the knife carrier such that the back span extends across the longitudinal slot and the catch member extends into the longitudinal slot.

In some embodiments, the first and second legs extend through openings in the knife carrier into the central bore.

In certain embodiments, each of the first and second legs includes an end and the ends of the first and second legs are bent to secure the first and second legs within the central bore.

In embodiments, the locking member includes a torsion spring that is pivotably supported on the knife carrier.

In some embodiments, the torsion spring includes spaced legs and a back span that extends between the spaced legs, wherein each of the spaced legs includes a loop.

In certain embodiments, a pivot member supported on the outer surface of the knife carrier and is received within the loops of the first and second legs.

In embodiments, the back span extends across the longitudinal slot and the catch member extends into the longitudinal slot.

In some embodiments, the circular stapling device includes a handle assembly.

In certain embodiments, the elongate body is adapted to be coupled to a robotic surgical system.

BRIEF DESCRIPTION OF THE DRAWINGS

Various embodiments of the presently disclosed reload assembly are described herein below with reference to the drawings, wherein:

FIG. 4 is a perspective view from the proximal end of a knife carrier of the reload assembly shown in FIG. 3 with a locking spring secured to the knife carrier;

FIG. 5 is a perspective view from the distal end of the knife carrier shown in FIG. 4 with the locking spring secured to the body of the knife carrier;

FIG. 13 is an enlarged view of the indicated area of detail shown in FIG. 12;

FIG. 14 is an enlarged view of the area of detail shown in FIG. 13 with parts separated;

DETAILED DESCRIPTION OF EMBODIMENTS

Figure 1:
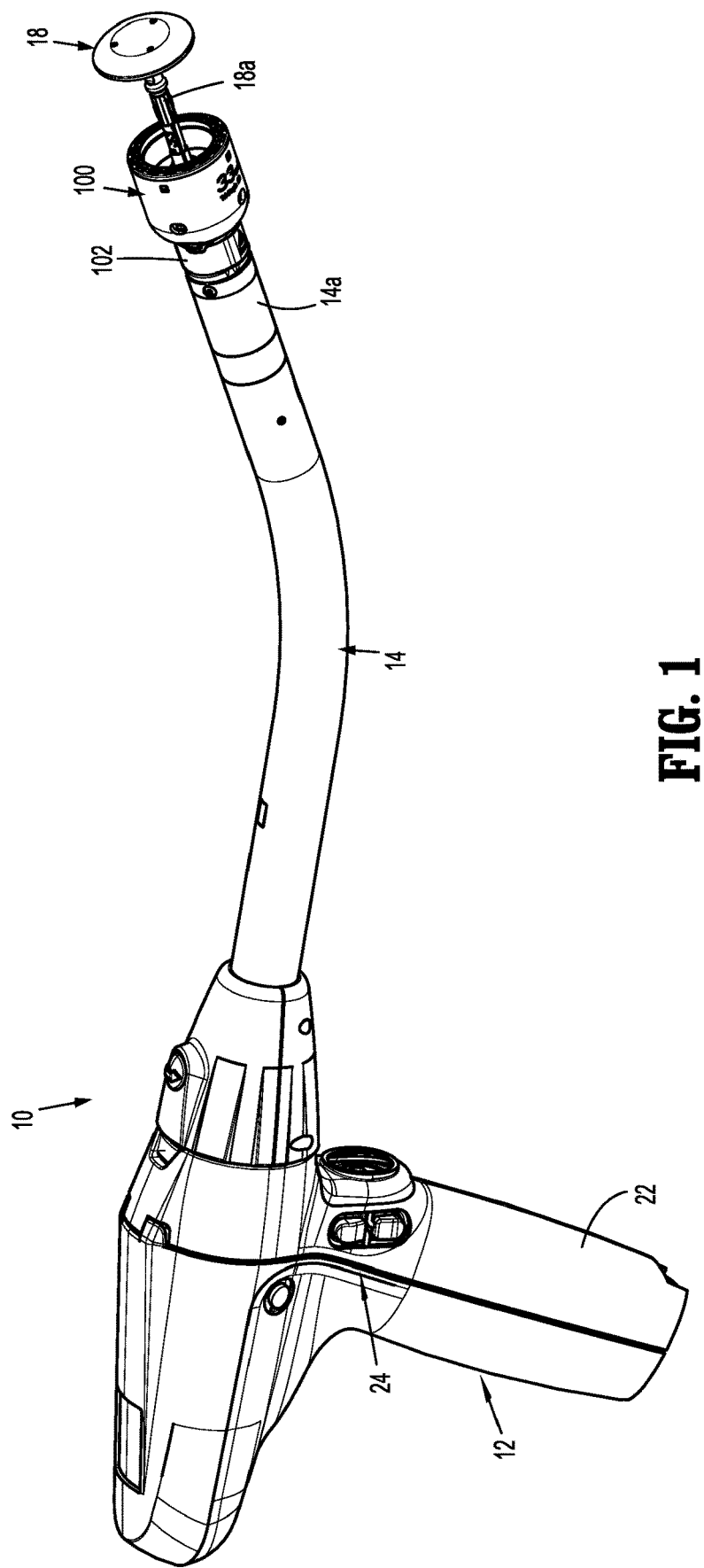
FIG. 1 is a side perspective view of a circular stapling device including an exemplary embodiment of the presently disclosed reload assembly in accordance with the present disclosure.

The presently disclosed reload assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 2:
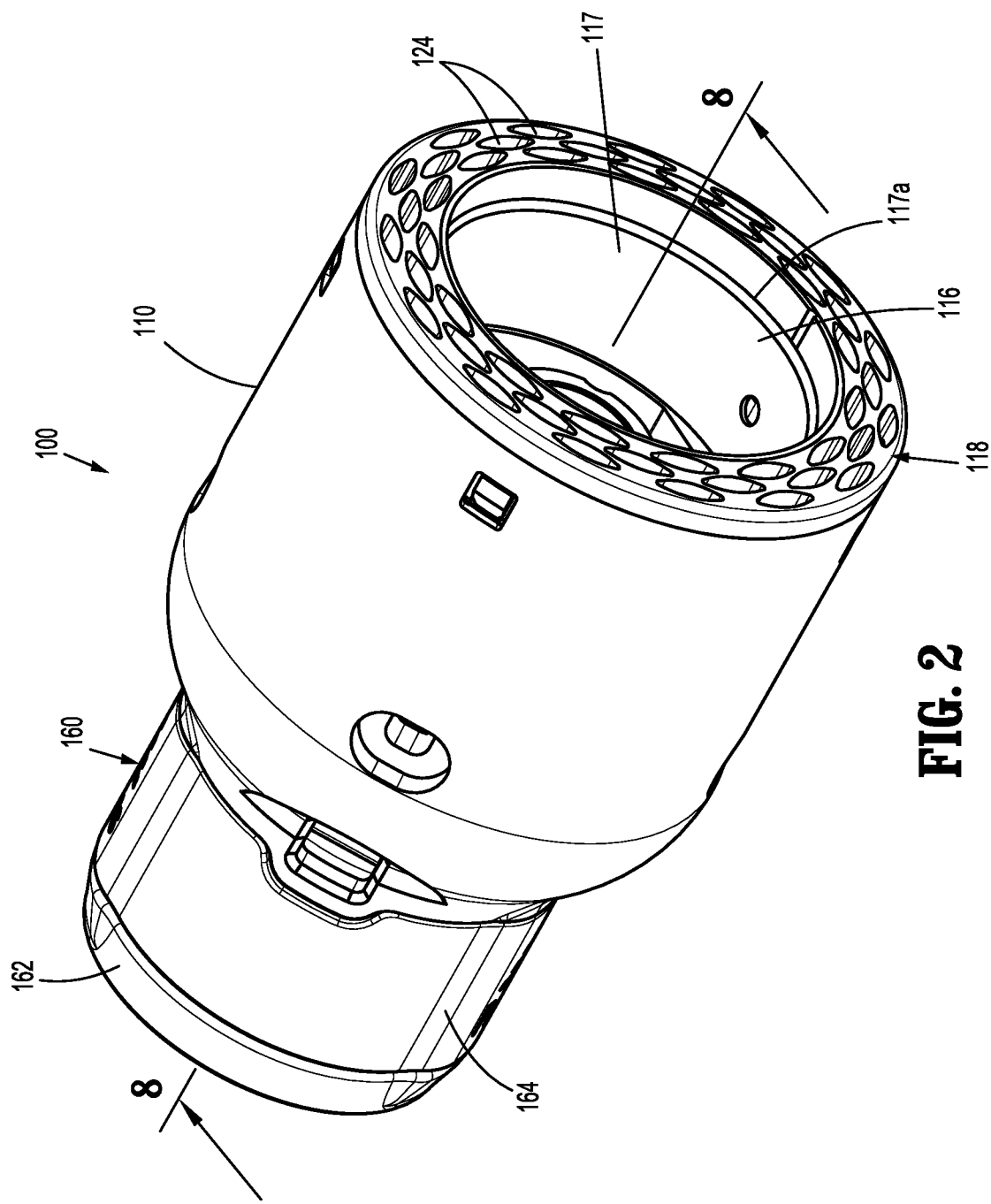
FIG. 2 is a side perspective view of the reload assembly of FIG. 1.

FIGS. 1 and 2 illustrate a circular stapling device 10 including an exemplary embodiment of the presently disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. The reload assembly 100 includes a proximal portion 102 (FIG. 1) that is releasably coupled to a distal portion 14a of the elongate body 14. The handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in the '943 patent), U.S. Pat. No. 9,023,014 (the '014 patent), and U.S. Publication Nos. 2018/0125495, and 2017/0340351 which are incorporated herein by reference in their entirety. Alternately, it is envisioned that the present disclosure could also be incorporated into a manually powered stapling device such as taught in U.S. Pat. No. 7,303,106 (the '106 patent) or a stapling device that is configured for use with a robotic system that does not include a handle assembly. For example, the elongate body can be adapted to engage a robotic surgical system in a manner similar to other robotic instruments known in the art. The '106 patent is also incorporated herein by reference in its entirety.

Figure 3:
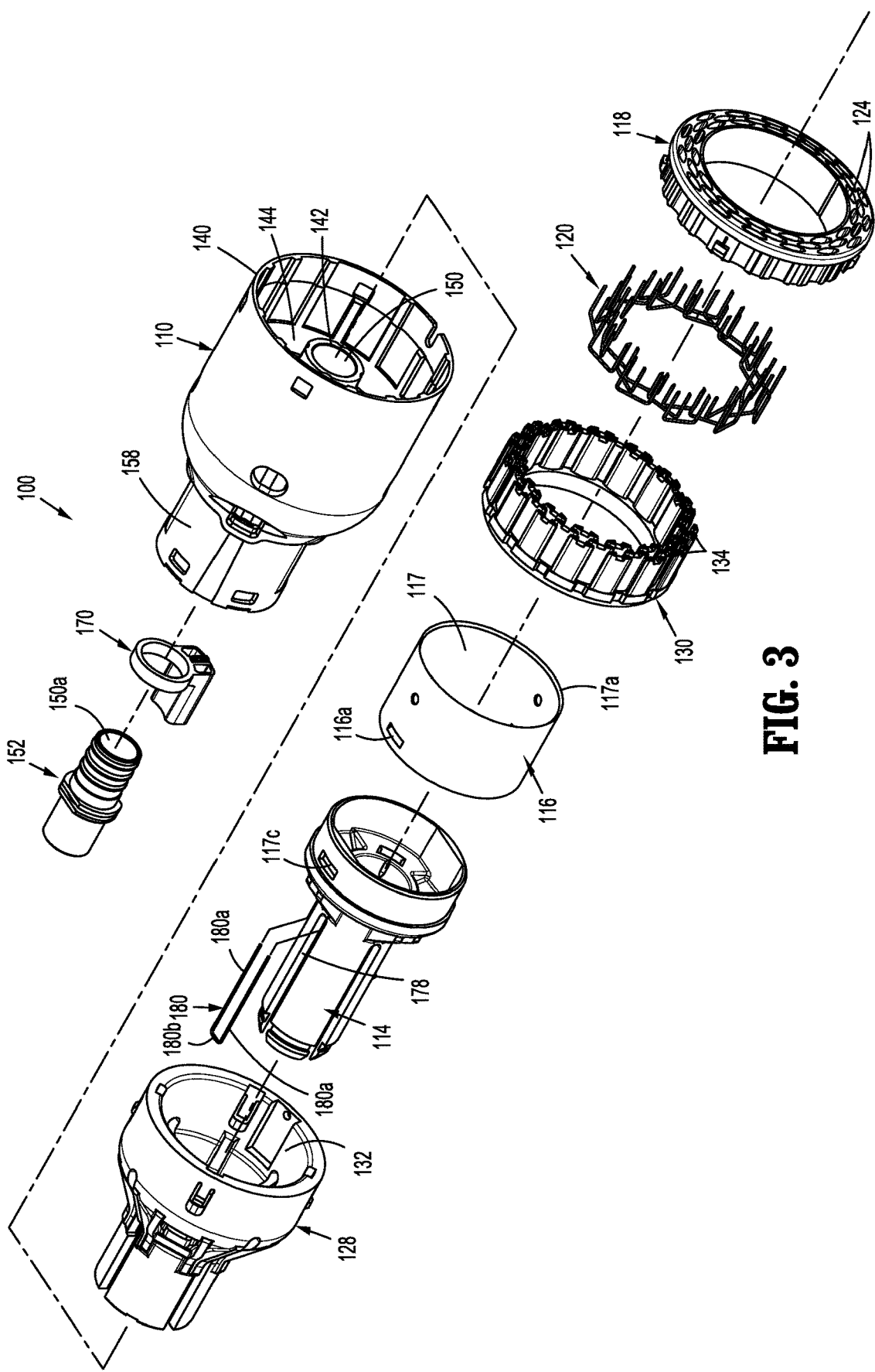
FIG. 3 is an exploded side perspective view of the reload assembly of FIG. 2.

Referring to FIGS. 2 and 3, the reload assembly 100 includes a shell housing 110, a pusher assembly 112 (FIG. 8), a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one of the plurality of staples 120. The pusher assembly 112 includes an annular pusher 128 (FIG. 3) and a staple pushing member 130 that together define a longitudinal through bore 132. The pusher 128 has a distal portion that abuts a proximal portion of the staple pushing member 130 such that distal movement of the pusher 128 within the shell housing 110 causes distal movement of the staple pushing member 130. The staple pushing member 130 of the reload 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 130 is moved from a retracted position to an advanced position within the shell housing 110.

The shell housing 110 includes an outer housing portion 140 and an inner housing portion 142 that are spaced from each other to define an annular cavity 144 between the inner and outer housing portions 140 and 142. The pusher assembly 112 (FIG. 8), the knife carrier 114, and the annular knife 116 are movable within the annular cavity 144 between retracted and advanced positions. The pusher assembly 112 is movable from its retracted position to its advanced position independently of the knife carrier 114 and annular knife 116 to eject the staples 120 from the staple cartridge 118. The annular knife 116 is supported about an outer surface of the knife carrier 114 and defines a cylindrical cavity 117 and a distal cutting edge 117a. In embodiments, the knife 116 includes projections 116a (FIG. 8) that are received in openings 117c (FIG. 8) in the knife carrier 114 to secure the knife 116 about the knife carrier 114. Alternately, other fastening techniques may be used to secure the knife 116 to the knife carrier 114. After the pusher assembly 112 is moved from its retracted position to its advanced position, the knife carrier 114 can be moved from its retracted position to its advanced position to cut tissue positioned radially inward of the staple cartridge 118.

The inner housing portion 142 of the shell housing 110 defines a through bore 150 (FIG. 3) that receives an anvil shaft 18a (FIG. 1) of the anvil assembly 18. For a more detailed description of an exemplary anvil assembly 18, see, e.g., the '106 Patent. The through bore 150 has a proximal portion that receives a bushing 152 that defines a through bore 150a that is coaxial and forms an extension of the through bore 150 of the inner housing portion 142. In embodiments, the bushing 152 is formed of a high strength material, e.g., metal, to provide added strength to the inner housing portion 142 of the shell housing 110.

The shell housing 110 includes a proximal portion 158 (FIG. 3) that supports a coupling mechanism 160 (FIG. 2) that is operable to releasably couple the reload assembly 100 to the adaptor assembly 14 of the stapling device 10 (FIG. 1) to facilitate replacement of the reload assembly 100 and reuse of the stapling device 10. The coupling mechanism 160 includes a retaining member 162 and a coupling member 164. The coupling member 164 is received about the proximal portion 158 (FIG. 3) of the shell housing 110 and is configured to engage the distal portion 114a of the adaptor assembly 14 to couple the adaptor assembly 14 to the reload assembly 100. It is envisioned that other coupling mechanisms can be used to secure the reload assembly 100 to the adaptor 14.

The reload assembly 100 may include an e-prom 170 (FIG. 3) that is supported on the shell housing 110. As is known in the art, the e-prom can communicate with the adaptor assembly 14 to provide information to the adaptor assembly 14 and the handle assembly 12 related to characteristics of the reload assembly 10.

Referring to FIGS. 3-5, the knife carrier 114 is movably positioned within the through bore 132 (FIG. 8) of the pushing assembly 112 between its retracted and advanced positions and defines a stepped central bore 172. The stepped central bore 172 includes a small diameter proximal portion 172a and a larger diameter distal portion 172b. The proximal portion 172a of the central bore 172 of the knife carrier 114 receives the inner housing portion 142 (FIG. 8) of the shell housing 110 such that the knife carrier 114 slides about the inner housing portion 142.

The knife carrier 114 defines an annular shoulder 176 (FIG. 5) that is positioned between the proximal portion 172a and the distal portion 172b of the central bore 172. The proximal portion 172a of the central bore 172 is defined by longitudinally extending body portions 173 (FIG. 4), which are separated from each other by longitudinal slots 178. The longitudinal slots 178 receive guide portions 179 (FIG. 6) of the shell housing 110 to limit the knife carrier 114 to longitudinal movement within the annular cavity 144 of the shell housing 110 as the knife carrier moves between its advanced and retracted positions. The shoulder 176 supports a resilient locking member 180 that that extends along an outer surface of the knife carrier 114 (FIG. 4) adjacent one of the longitudinal slots 178 as described in further detail below.

In embodiments, the locking member 180 includes an elongate spring arm that is substantially U-shaped and has first and second legs 180a and a back span 180b that extends between the legs 180a. When the locking member 180 is secured to the knife carrier 114, the back span 180b extends across one of the longitudinal slots 178 of the knife carrier 114 (FIG. 4). The locking member 180 is formed of a resilient material, e.g., spring steel, and is supported on an outer surface of the shoulder 176 of the knife carrier 114 to extend along the proximal portion of the knife carrier 114. In embodiments, the legs 180a of the locking member 180 extend through openings 182 (FIG. 4) defined in the annular shoulder 176 of the knife carrier 114 and include bent ends "B" (FIG. 5) to secure the locking member 180 to the knife carrier 114. It is envisioned that the knife carrier 114 may support one or more locking members 180, e.g., 1, 2, 3, etc.

Figure 6:
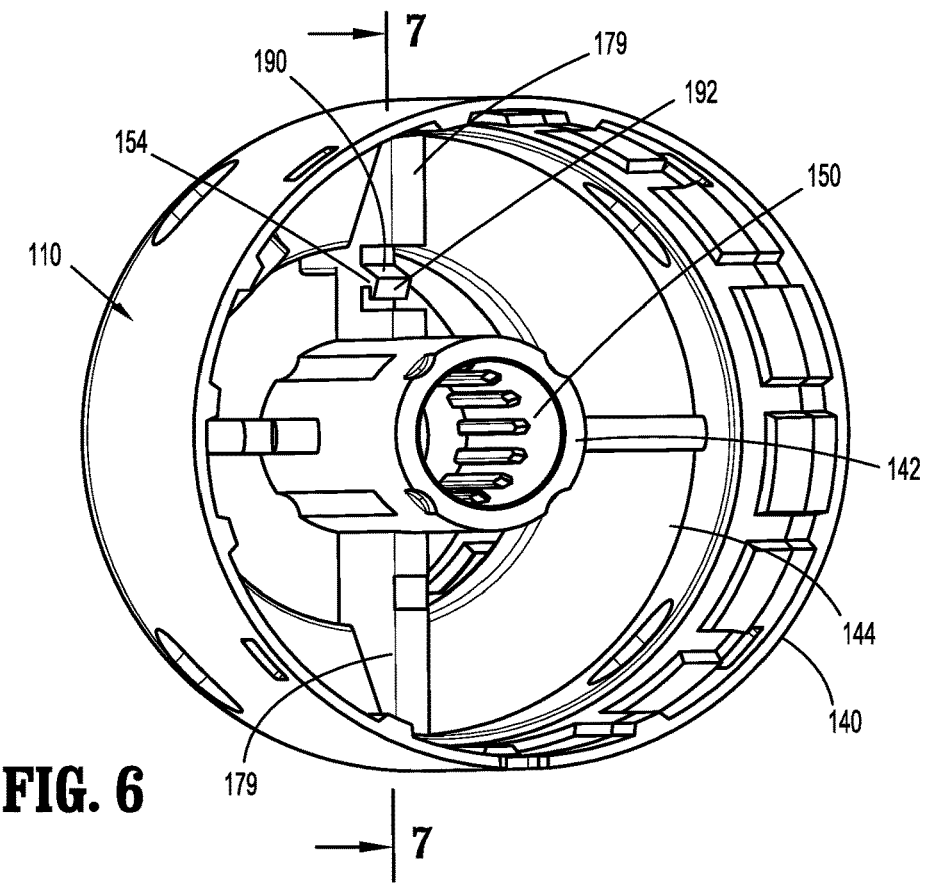
FIG. 6 is a perspective view from the distal end of the shell housing of the reload assembly shown in FIG. 3.
Figure 7:
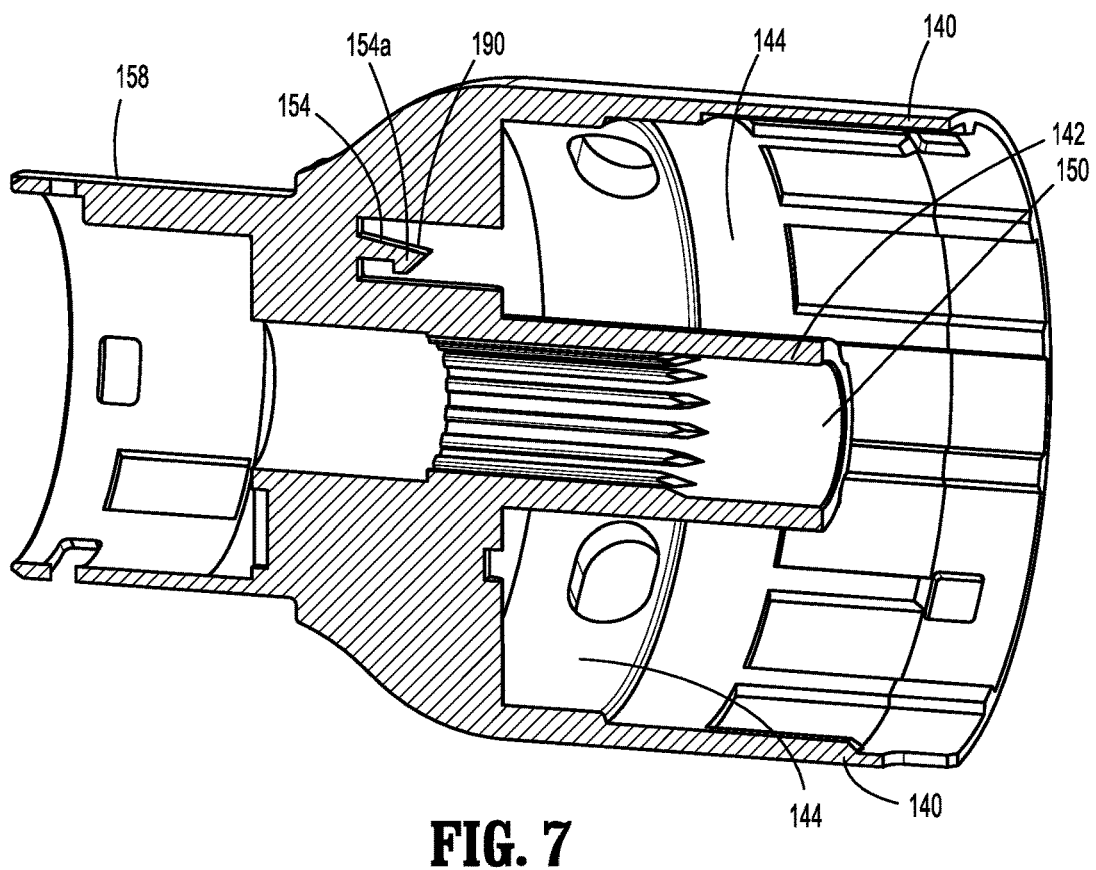
FIG. 7 is across-sectional view taken along section line 7-7 of FIG. 6.
Figure 8:
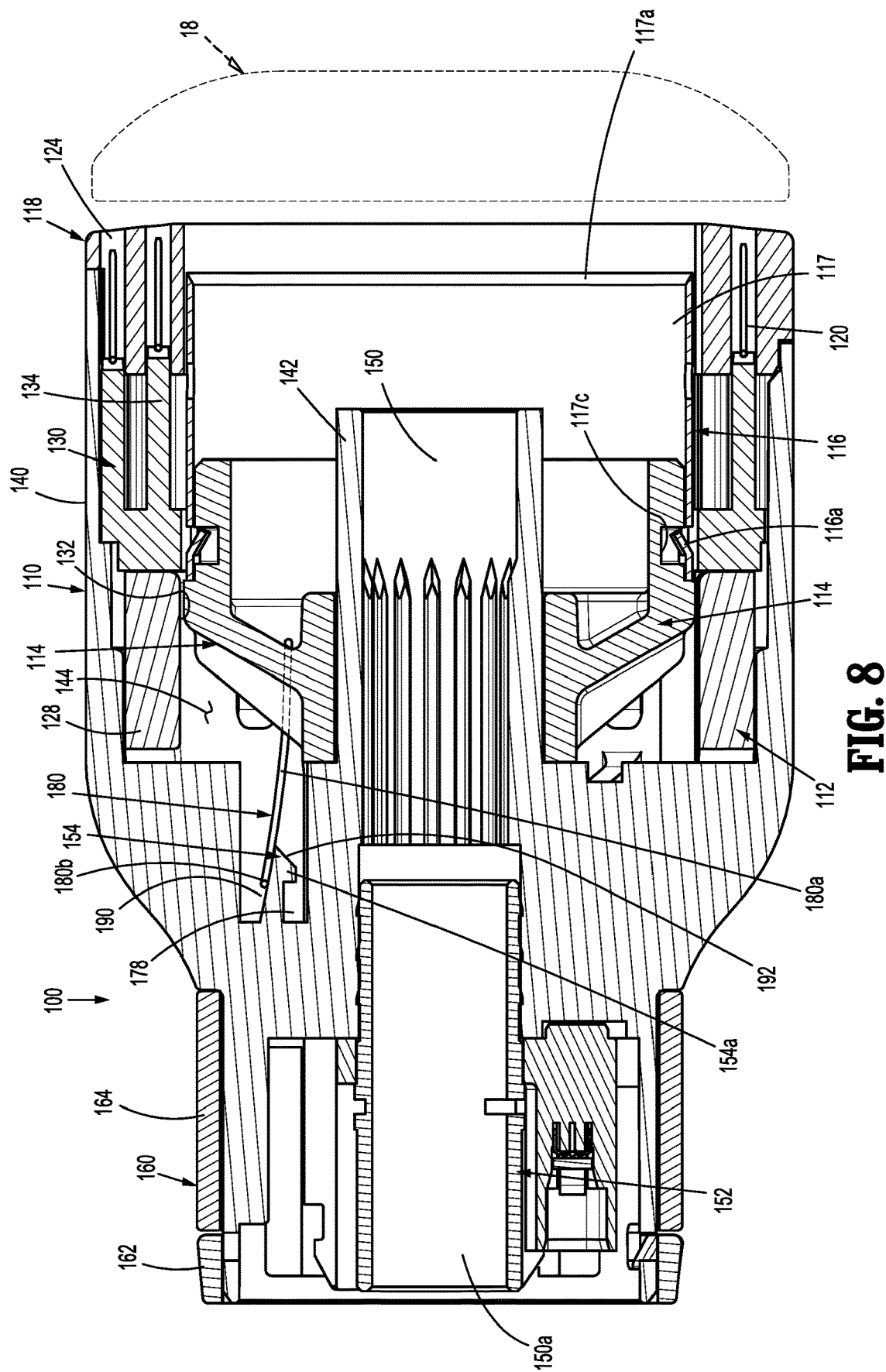
FIG. 8 is a cross-sectional view taken along section line 8-8 of FIG. 2 with the reload assembly in a pre-fired position with an anvil assembly shown in phantom.

Referring to FIGS. 6-8, the inner housing portion 142 of the shell housing 110 includes a catch member 154 that is positioned in the annular cavity 144 between the inner and outer housing portions 140 and 142, respectively. The catch member 154 includes a cantilevered hook-portion 154a that extends into a respective longitudinal slot 178 of the knife carrier 114 (FIG. 8) and engages the back span 180b of the locking member 180 when the knife carrier 142 is in its retracted position and the locking member 154 is in an unbiased state as discussed in detail below. The catch member 154 includes a cam surface 190 that is positioned radially outwardly of the hook-portion 154a and supports the locking member 180 when the locking member 180 is in a biased state (FIG. 8) disengaged from the hook-portion 154a. The locking member 180 is in the biased state when the knife carrier 114 is in a retracted position before the reload assembly 100 has been fired. The hooked-portion 154a of the catch member 154 includes a face 192 that is tapered radially inwardly in the proximal direction towards the inner housing portion 142 of the shell housing 110.

Referring to FIG. 8, when the knife carrier 114 is in the retracted position, prior to firing of the reload assembly 100, the back span 180a of the locking member 180 is supported on the cam surface 190 of the catch member 154. In this position, the locking member 180 is in a biased state and is flexed radially outwardly of the hook-portion 154a of the catch member 154.

Figure 9:
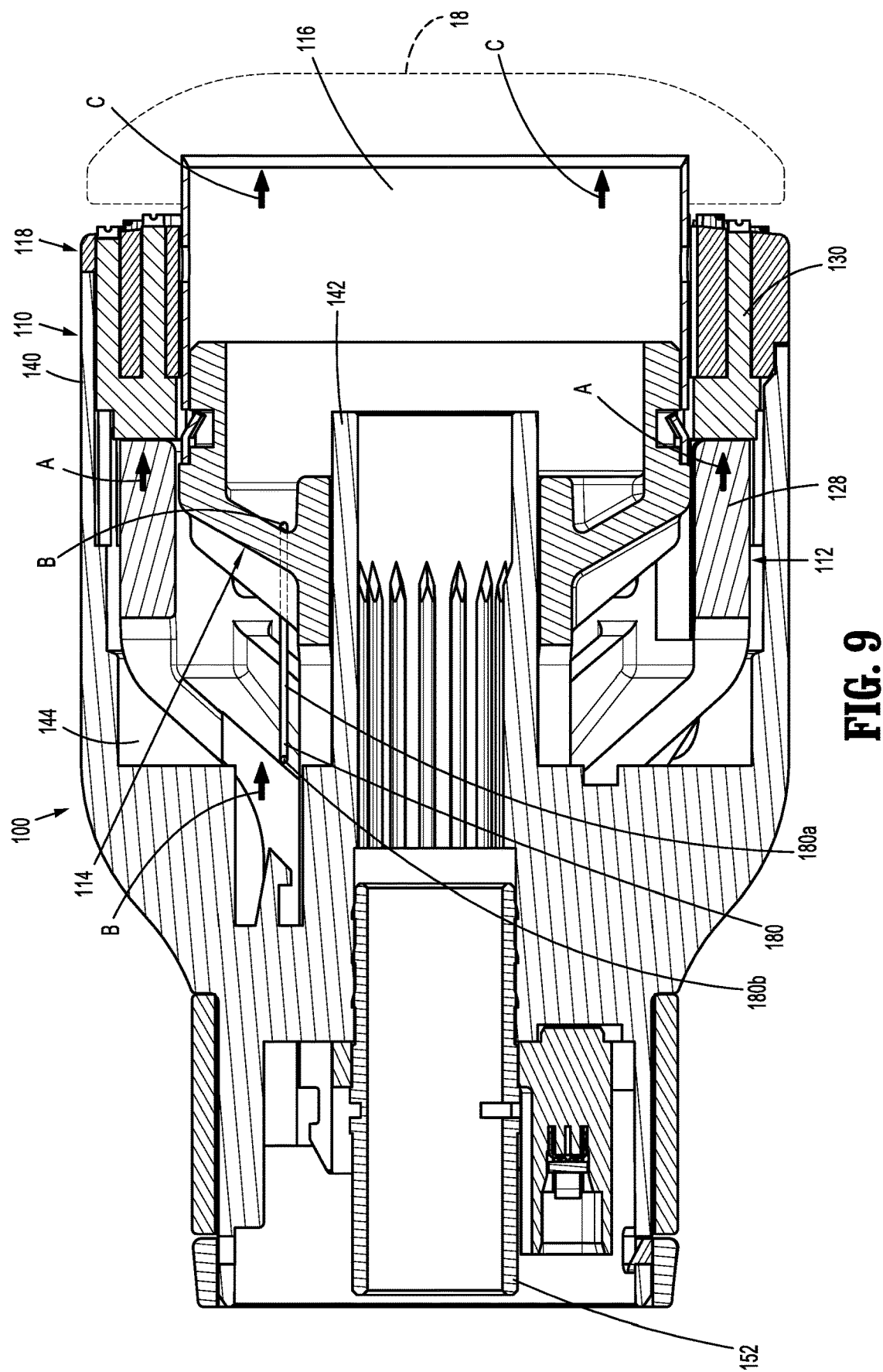
FIG. 9 is a cross-sectional view taken along section line 8-8 of FIG. 2 with the reload assembly in a fired position.

Referring to FIG. 9, when the stapling device 10 is actuated via actuation of the handle assembly 12 (FIG. 1) to fire staples 120 (FIG. 8), the pusher assembly 112 including the annular pusher 128 and the staple pushing member 130 are advanced in the direction indicated by arrows "A" towards the anvil assembly 18 to form the staples 120 in tissue clamped between the staple cartridge 118 and the anvil 18.

After the staples are fired, the knife carrier 114 of the reload assembly 100 is advanced in the direction indicated by arrow "B" to advance the annular knife 116 in the direction indicated by arrows "C". As the knife carrier 114 and annular knife 116 are advanced, the back span 180b of the locking member 180 which is coupled to the outer surface of the knife carrier 114, slides distally along and off of the cam surface 190 of the catch member 154. When the back span 180b passes off the cam surface 190 to a position distally of the catch member 154, the locking member 154 returns to an unbiased state in which the back span 180b is axially aligned with the tapered face 192 of the hook-portion 154a of the catch member 154. As the knife carrier 114 is advanced within the annular cavity 144 of the shell housing 110, the annular knife 116 is advanced into the anvil assembly 118 to cut tissue clamped between the anvil assembly 18 and the staple cartridge 118.

Figure 10:
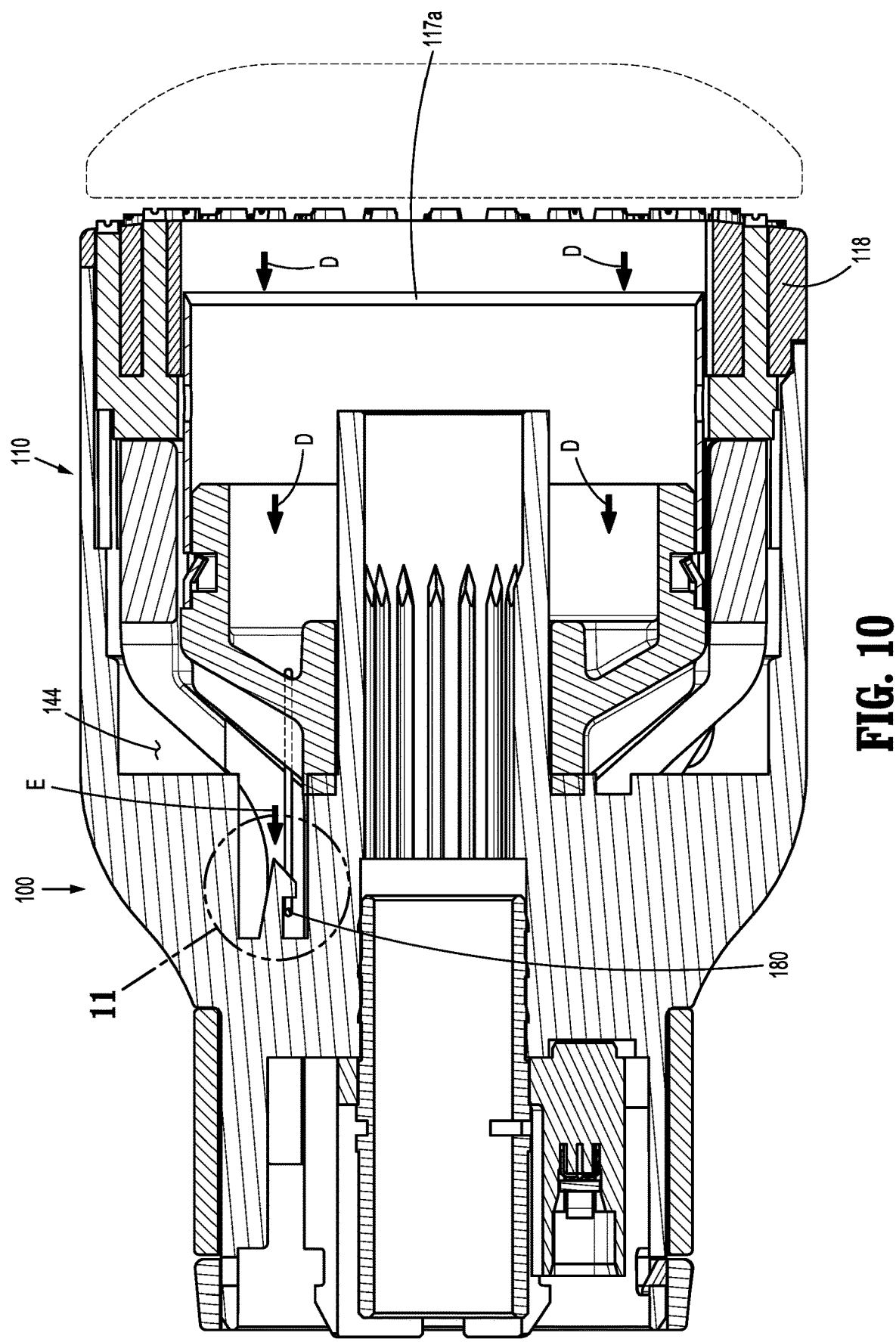
FIG. 10 is a cross-sectional view taken along section line 8-8 of FIG. 2 after the reload assembly has been fired and returned to the retracted position.
Figure 11:
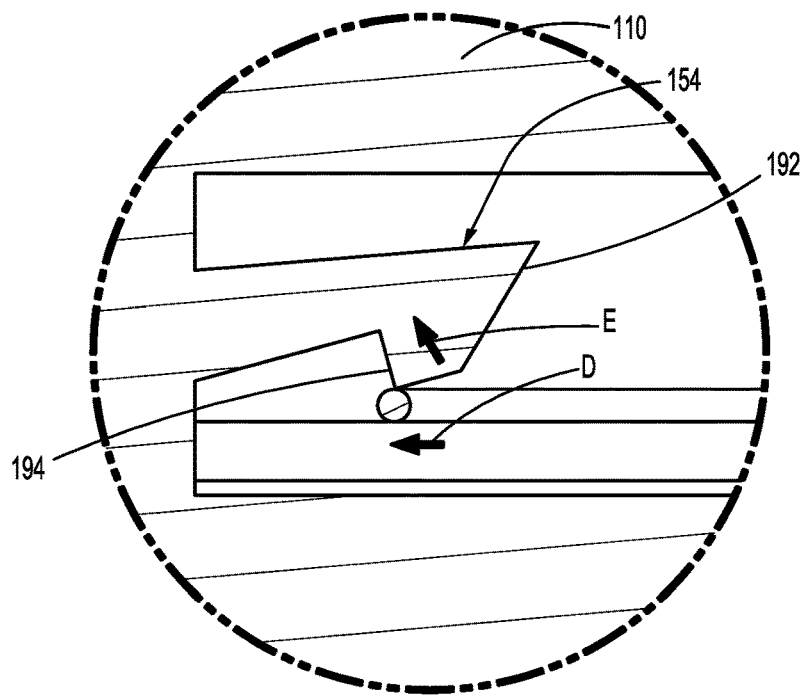
FIG. 11 is an enlarged view of the indicated area of detail shown in FIG. 10.
Figure 12:
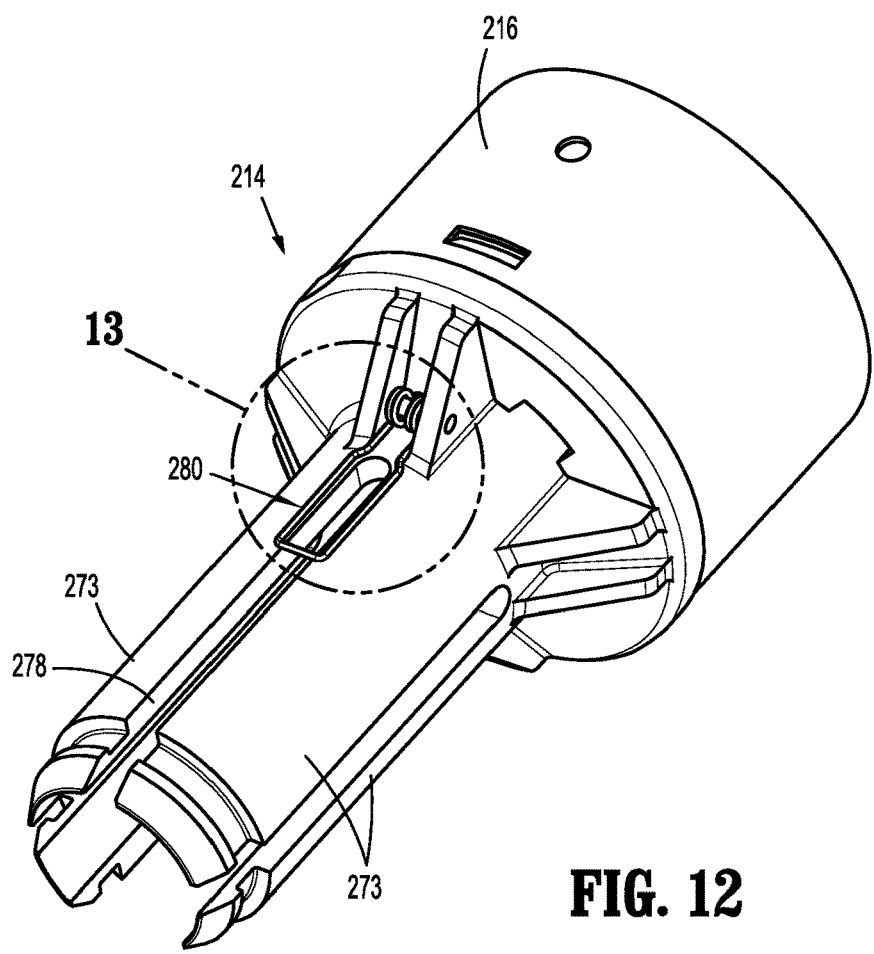
FIG. 12 is a side perspective view from the distal end of an alternate embodiment of the knife carrier of the reload assembly shown in FIG. 2.

Referring to FIGS. 10 and 11, when the knife carrier 114 is moved proximally within the annular cavity 144 of the shell housing 110 to its retracted position in the direction indicated by arrows "D", the annular knife 116 is withdrawn into the shell housing 110 and the cutting edge 117a is shielded by the staple cartridge 118. When the knife carrier 114 nears its retracted position, the back span 180b of the locking member 180 which is moving in the direction indicated by arrow "D" in FIG. 11 engages the tapered face 192 of the catch member 154 and biases the catch member 154 upwardly in the direction indicated by arrow "E" such that the back span 180b passes beneath the catch member 154 to a position behind a stop surface 194 of the hook-portion 154a of the catch member 154. In this position, engagement between the locking member 180 and the catch member 154 obstructs movement of the knife carrier 114 and knife 116 back towards the advanced position. As such, the annular knife 116 is retained in its retracted position within the shell housing 110 to facilitate manipulation and disposal of the reload assembly by the clinician.

Figure 15:
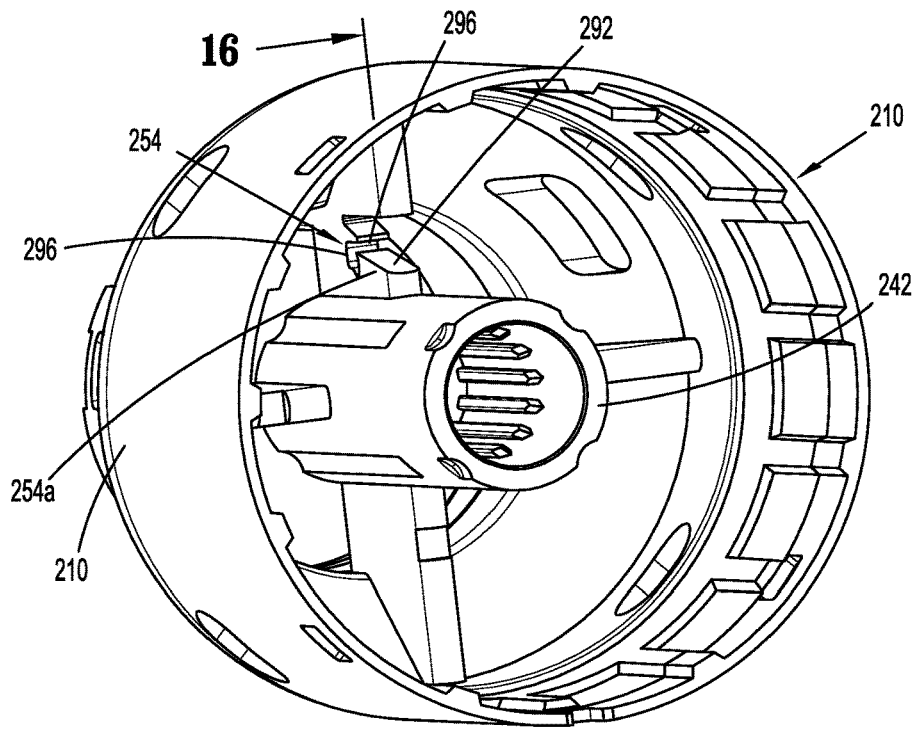
FIG. 15 is a perspective view from the distal end of an alternative embodiment of the shell housing of the reload assembly shown in FIG. 2.
Figure 16:
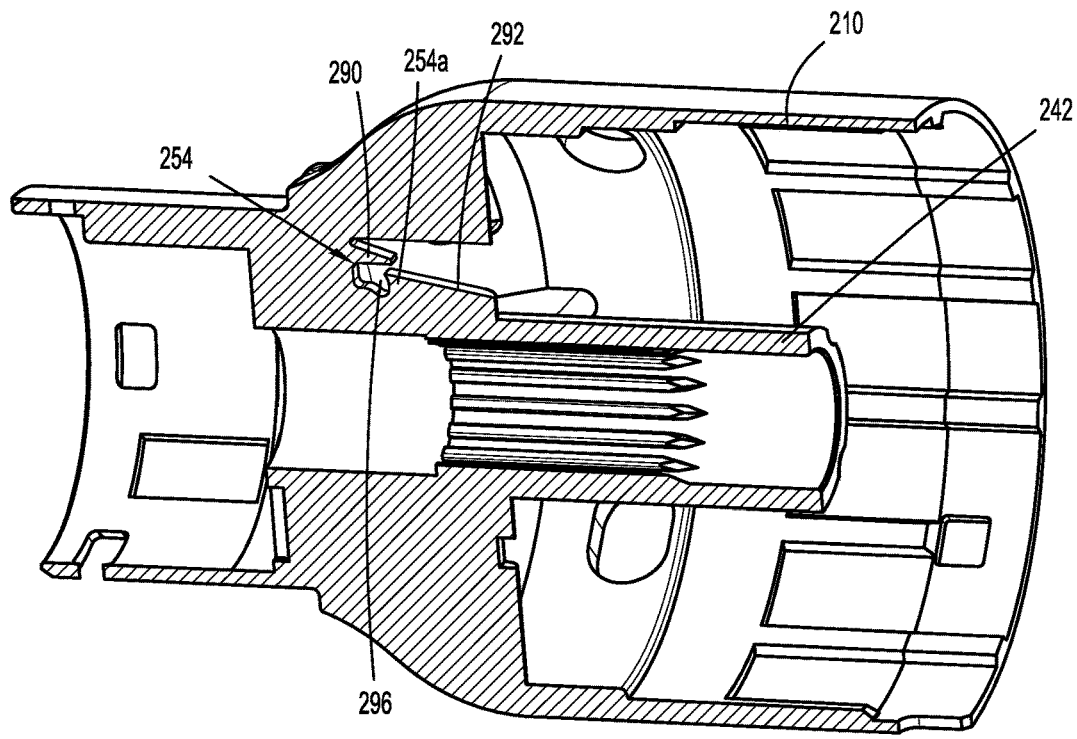
FIG. 16 is a cross-sectional view taken along section line 16-16 of FIG. 15.
Figure 17:
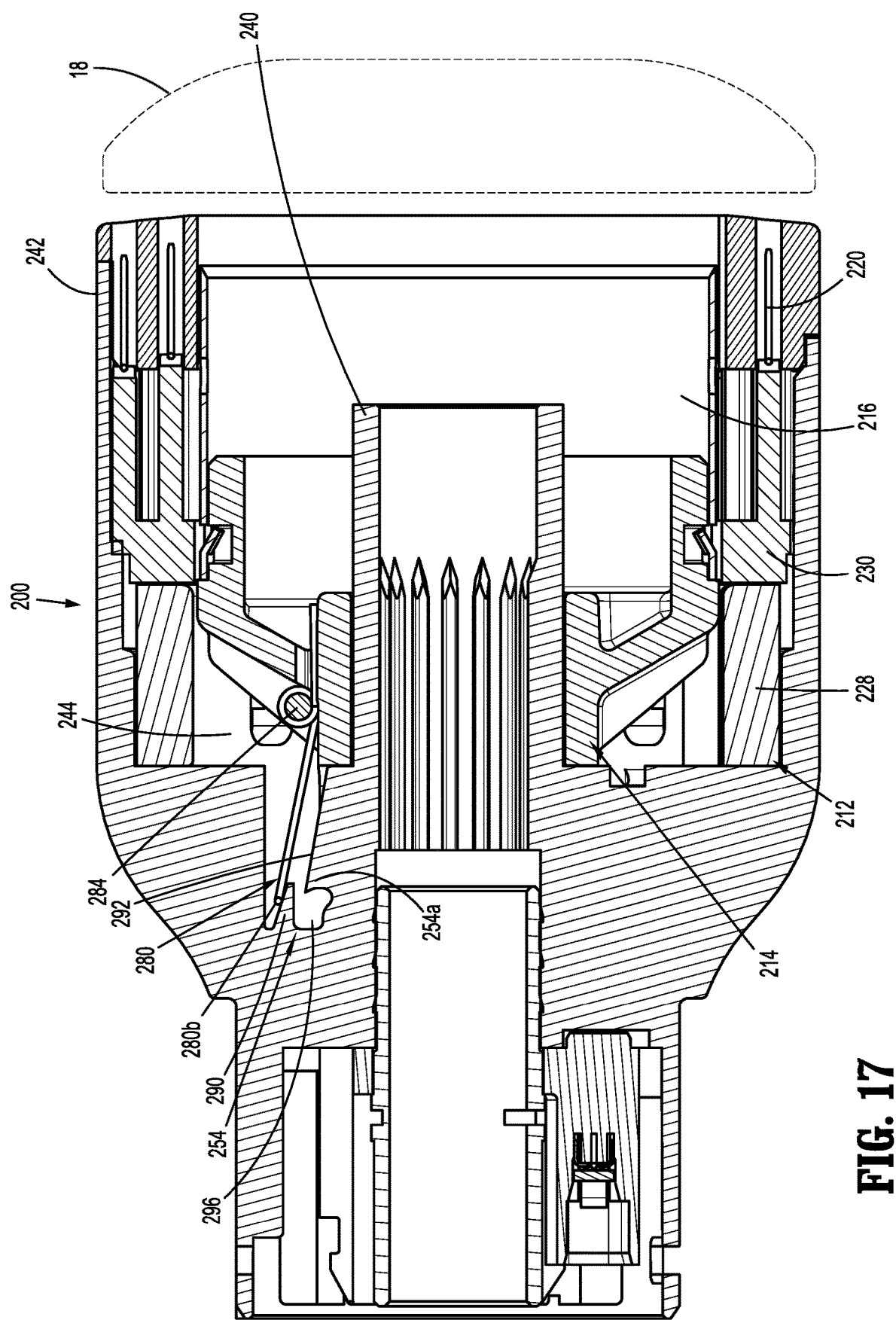
FIG. 17 is a cross-sectional view of the reload assembly shown in FIG. 2 including the alternative embodiments of the knife carrier and shell housing with the reload assembly in a pre-fired position and an anvil assembly shown in phantom.

FIGS. 13-19 illustrate an alternative embodiment of the presently disclosed reload assembly 200 (FIG. 17). The reload assembly 200 is similar to the reload assembly 100 except the configurations of the catch member 154 (FIG. 10) and locking member 180 (FIG. 3) have been modified. All of the remaining components of the reload assembly 200 are as described with respect to reload assembly 100. Accordingly, only the modifications will be described in detail herein.

Referring to FIGS. 13 and 14, the locking member 280 is in a form of a torsion spring and includes spaced legs 280a and a back span 280b. A central portion of each of the legs 280a defines a loop 282. The loops 282 receive a pivot member 284 that is supported between ribs 286 that are formed on an outer surface of the knife carrier 214. As discussed above in regard to the locking member 180, the locking member 280 is supported on an outer surface of the knife carrier 214 such that the back span 280b of the locking member 280 extends across one of the longitudinal slots 278 defined between longitudinal body portions 273 of the knife carrier 214.

Referring to FIGS. 15 and 16, the inner housing portion 242 of the shell housing 210 includes a catch member 254 that is positioned in the annular cavity 244 between the inner and outer housing portions 240 and 242, respectively. The catch member 254 includes a hook-portion 254a that extends through a respective longitudinal slot 278 in the knife carrier 214 to a position radially outward of the knife carrier 114. The catch member 254 engages the back span 280b of the locking member 280 when the knife carrier 242 is in a retracted position and the catch member 254 is in an unbiased state as discussed in detail below to obstruct advancement of the knife carrier 214. The catch member 254 also includes a cam member 290 that is positioned radially outwardly of the hook-portion 254a of the catch member 254. The cam member 290 supports the locking member 280 in a biased state outwardly of the hook portion 254a of the catch member 254 when the knife carrier 214 is in a retracted position before the reload assembly 200 has been fired. The hooked-portion 254a of the catch member 254 includes a tapered surface 292 that is positioned within a longitudinal slot 278 and is tapered radially outwardly in the proximal direction. The hooked portion 254a of the catch member 254 and the cam member 290 define a pocket 296.

Referring to FIG. 17, when the knife carrier 214 is in the retracted position, prior to firing of the reload assembly 200, the back span 280b of the locking member 280 is supported on the cam member 290 of the catch member 254. In this position, the locking member 280 is in a biased state and is flexed radially outwardly of the hook-portion 254a of the catch member 254 such that the back span 280b of the locking member 280 is positioned outside of the pocket 296.

Figure 18:
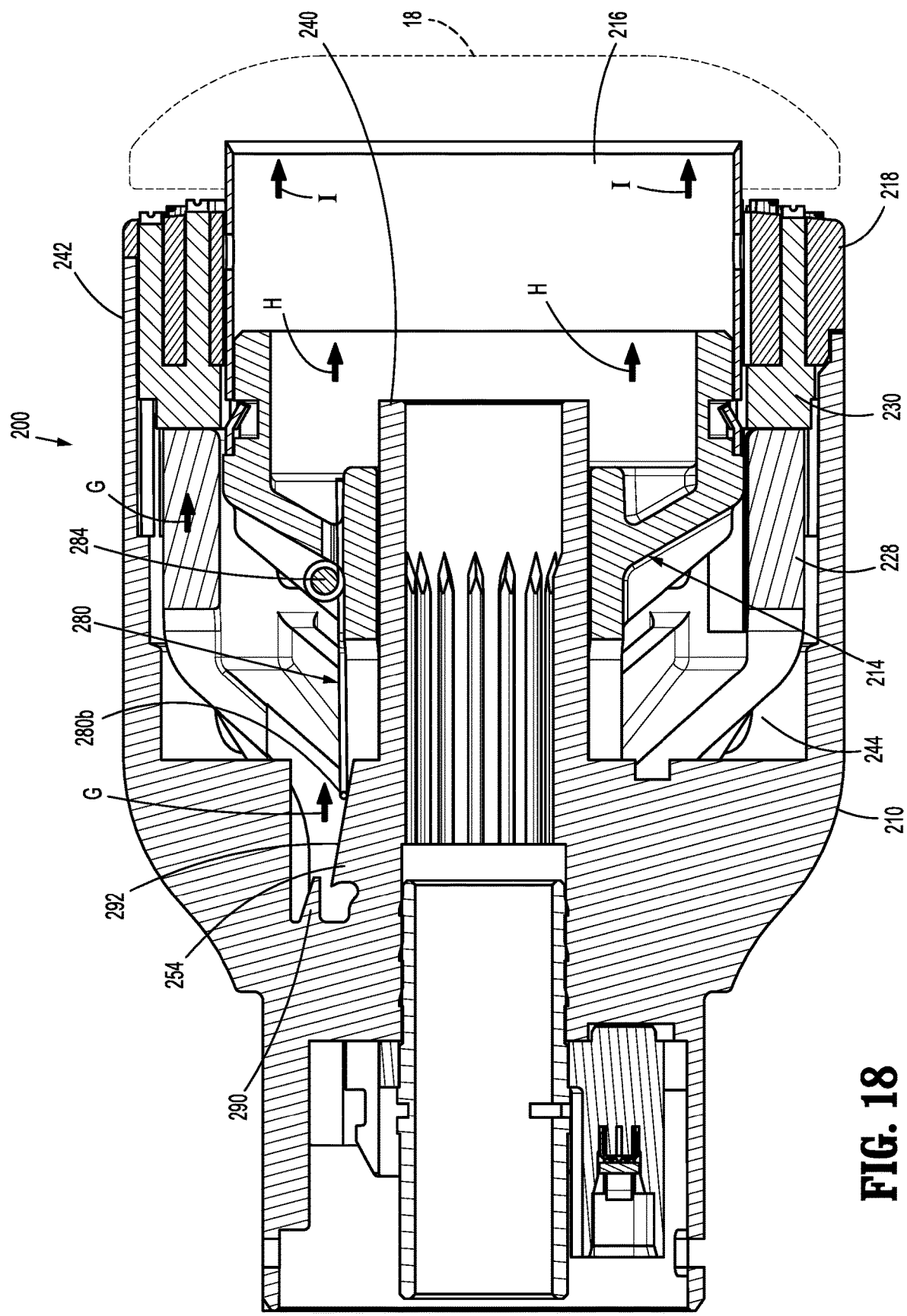
FIG. 18 is the cross-sectional view of the reload assembly shown in FIG. 17 with the reload assembly in a fired position.

Referring to FIG. 18, when the stapling device 10 (FIG. 1) is actuated via actuation of the handle assembly 12 to fire staples 220 (FIG. 17), the pusher assembly 212 including the annular pusher 228 and the staple pushing member 230 are advanced in the direction indicated by arrows "G" towards the anvil assembly 18 to form the staples 220 in tissue clamped between the staple cartridge 218 and the anvil 18.

After the staples are fired, the knife carrier 214 of the reload assembly 200 is advanced in the direction indicated by arrow "H" to advance the annular knife 216 in the direction indicated by arrows "I". As the knife carrier 214 and annular knife 216 are advanced, the back span 280b of the locking member 280 which is coupled to the outer surface of the knife carrier 214 about pivot member 284 slides distally along and off of the cam surface 290 of the catch member 254. When the back span 280b passes off the cam member 290 to a position distally of the catch member 254, the locking member 280 returns to an unbiased state in which the back span 280b is axially aligned with the tapered surface 292 of the hook-portion 254a of the catch member 254. As the knife carrier 214 is advanced within the annular cavity 244 of the shell housing 210, the annular knife 216 is advanced into the anvil assembly 18 to cut tissue clamped between the anvil assembly 18 and the staple cartridge 218.

Figure 19:
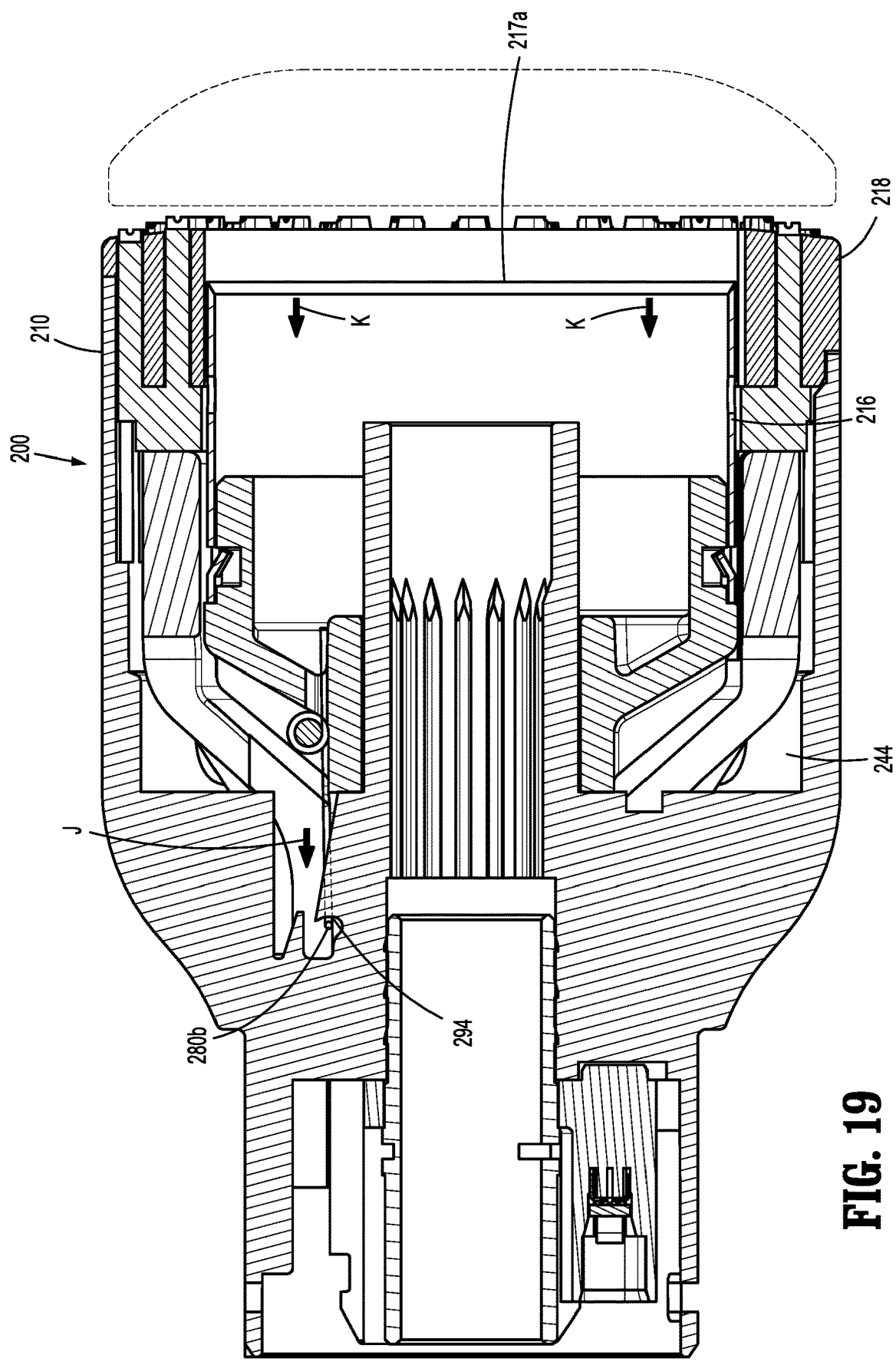
FIG. 19 the cross-sectional view of the reload assembly shown in FIG. 17 after the reload assembly has been fired and the reload assembly is returned to the retracted position.

Referring to FIG. 19, when the knife carrier 214 is moved proximally within the annular cavity 244 of the shell housing 210 to its retracted position in the direction indicated by arrow "J", the annular knife 216 is withdrawn into the shell housing 210 in the direction indicated by arrows "K" and the cutting edge 217a of the knife 216 is shielded by the staple cartridge 218. When the knife carrier 214 nears its retracted position, the back span 280b of the locking member 280 engages the tapered surface 292 of the hook-portion 254a of the catch member 254 and is biased outwardly along the tapered surface 192 and over the hook-portion 254a. When the back span 280b passes proximally over the hook-portion 254a, the back span 280b snaps inwardly into the recess 296 to a position behind a stop surface 294 of the hook-portion 254a of the catch member 254. In this position, engagement between the locking member 280 and the catch member 254 obstructs movement of the knife carrier 214 and knife 216 back towards the advanced position. As such, the annular knife 216 is retained in its retracted position within the shell housing 210 to facilitate manipulation and disposal of the reload assembly 200 by the clinician.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
    a shell housing including an inner housing portion and an outer housing portion, the inner housing portion spaced from the outer housing portion to define an annular cavity between the inner and outer housing portions;
    a staple cartridge supported on a distal portion of the shell housing, the staple cartridge having a plurality of staple pockets, each of the staple pockets receiving a staple;
    a pusher supported within the annular cavity, the pusher movable between a retracted position and an advanced position to eject the staples from the staple cartridge;
    a knife carrier including a body defining a longitudinal axis and supporting a knife, the body of the knife carrier defining a central bore and a longitudinal slot communicating with the central bore, the inner housing portion of the shell housing being positioned within the central bore of the knife carrier such that the knife carrier is movable about the inner housing portion of the shell housing between advanced and retracted positions;
    a catch fixedly secured to the shell housing and positioned within the annular cavity of the shell housing; and
    a locking member supported on the knife carrier, the locking member movable from a biased state to an unbiased state, wherein in the unbiased state, the locking member is positioned to engage the catch to retain the knife carrier in the retracted position.

2. The reload assembly of claim 1, wherein the catch includes a hook-portion that extends into the longitudinal slot.

3. The reload assembly of claim 1, wherein the catch includes a cam surface and the locking member is supported on the cam surface in the biased state when the knife carrier is in the retracted position prior to firing of the reload assembly.

4. A reload assembly comprising:
    a shell housing including an inner housing portion and an outer housing portion, the inner housing portion spaced from the outer housing portion to define an annular cavity between the inner and outer housing portions;
    a staple cartridge supported on a distal portion of the shell housing, the staple cartridge having a plurality of staple pockets, each of the staple pockets receiving a staple;
    a pusher supported within the annular cavity, the pusher movable between a retracted position and an advanced position to eject the staples from the staple cartridge;
    a knife carrier including a body defining a longitudinal axis and supporting a knife, the body of the knife carrier defining a central bore and a longitudinal slot communicating with the central bore, the inner housing portion of the shell housing being positioned within the central bore of the knife carrier such that the knife carrier is movable about the inner housing portion of the shell housing between advanced and retracted positions;
    a catch positioned within the annular cavity of the shell housing; and
    a locking member supported on the knife carrier, the locking member movable from a biased state to an unbiased state, wherein in the unbiased state, the locking member is positioned to engage the catch to retain the knife carrier in the retracted position
    wherein the catch includes a hook-portion that extends into the longitudinal slot and the locking member includes a U-shaped spring arm having first and second legs and a back span extending between the first and second legs.

5. The reload assembly of claim 4, wherein the spring arm is supported on an outer surface of the knife carrier such that the back span extends across the longitudinal slot and the catch member extends into the longitudinal slot.

6. The reload assembly of claim 5, wherein the first and second legs extend through openings in the knife carrier into the central bore.

7. The reload assembly of claim 6, wherein each of the first and second legs includes an end and the ends of the first and second legs being bent to secure the first and second legs within the central bore.

8. A reload assembly comprising:
    a shell housing including an inner housing portion and an outer housing portion, the inner housing portion spaced from the outer housing portion to define an annular cavity between the inner and outer housing portions;
    a staple cartridge supported on a distal portion of the shell housing, the staple cartridge having a plurality of staple pockets, each of the staple pockets receiving a staple;
    a pusher supported within the annular cavity, the pusher movable between a retracted position and an advanced position to eject the staples from the staple cartridge;
    a knife carrier including a body defining a longitudinal axis and supporting a knife, the body of the knife carrier defining a central bore and a longitudinal slot communicating with the central bore, the inner housing portion of the shell housing being positioned within the central bore of the knife carrier such that the knife carrier is movable about the inner housing portion of the shell housing between advanced and retracted positions;
    a catch positioned within the annular cavity of the shell housing; and
    a locking member supported on the knife carrier, the locking member movable from a biased state to an unbiased state, wherein in the unbiased state, the locking member is positioned to engage the catch to retain the knife carrier in the retracted position, wherein the catch includes a hook-portion that extends into the longitudinal slot and the locking member includes a torsion spring pivotably supported on the knife carrier.

9. The reload assembly of claim 8, wherein the torsion spring includes spaced legs and a back span extending between the spaced legs, each of the spaced legs including a loop.

10. The reload assembly of claim 9, further including a pivot member supported on the outer surface of the knife carrier, the pivot member received within the loops of the first and second legs.

11. The reload assembly of claim 9, wherein the back span extends across the longitudinal slot and the catch member extends into the longitudinal slot.

12. A circular stapling device comprising;
an elongate body having a proximal portion and a distal portion; and
a reload assembly supported on the distal portion of the elongate body, the reload assembly including:
  a shell housing including an inner housing portion and an outer housing portion, the inner housing portion spaced from the outer housing portion to define an annular cavity between the inner and outer housing portions;
  a staple cartridge supported on a distal portion of the shell housing, the staple cartridge having a plurality of staple pockets, each of the staple pockets receiving a staple;
  a pusher supported within the annular cavity, the pusher movable between a retracted position and an advanced position to eject the staples from the staple cartridge;
  a knife carrier including a body defining a longitudinal axis and supporting a knife, the body of the knife carrier defining a central bore and a longitudinal slot communicating with the central bore, the inner housing portion of the shell housing being positioned within the central bore of the knife carrier such that the knife carrier moves about the inner housing portion of the shell housing between advanced and retracted positions;
  a catch fixedly secured to the shell housing and positioned within the annular cavity of the shell housing; and
  a locking member supported on the knife carrier, the locking member movable from a biased state to an unbiased state, wherein in the unbiased state, the locking member is positioned to engage the catch to retain the knife carrier in the retracted position.

13. The circular stapling device of claim 12, wherein the catch of the reload assembly includes a hook-portion that extends into the longitudinal slot.

14. The circular stapling device of claim 13, wherein the catch of the reload assembly includes a cam surface and the locking member is supported on the cam surface in the biased state when the knife carrier is in the retracted position prior to firing of the reload assembly.

15. A circular stapling device comprising;
an elongate body having a proximal portion and a distal portion; and
a reload assembly supported on the distal portion of the elongate body, the reload assembly including:
  a shell housing including an inner housing portion and an outer housing portion, the inner housing portion spaced from the outer housing portion to define an annular cavity between the inner and outer housing portions;
  a staple cartridge supported on a distal portion of the shell housing, the staple cartridge having a plurality of staple pockets, each of the staple pockets receiving a staple;
  a pusher supported within the annular cavity, the pusher movable between a retracted position and an advanced position to eject the staples from the staple cartridge;
  a knife carrier including a body defining a longitudinal axis and supporting a knife, the body of the knife carrier defining a central bore and a longitudinal slot communicating with the central bore, the inner housing portion of the shell housing being positioned within the central bore of the knife carrier such that the knife carrier moves about the inner housing portion of the shell housing between advanced and retracted positions;
  a catch positioned within the annular cavity of the shell housing; and
  a locking member supported on the knife carrier, the locking member movable from a biased state to an unbiased state, wherein in the unbiased state, the locking member is positioned to engage the catch to retain the knife carrier in the retracted position, wherein the catch of the reload assembly includes a hook-portion that extends into the longitudinal slot and the locking member includes a U-shaped spring arm having first and second legs and a back span extending between the first and second legs.

16. The circular stapling device of claim 15, wherein the U-shaped spring arm is supported on an outer surface of the knife carrier such that the back span extends across the longitudinal slot, the catch member extending into the longitudinal slot.

17. The circular stapling device of claim 16, wherein the first and second legs extend through openings in the knife carrier into the central bore.

18. The circular stapling device of claim 17, wherein each of the first and second legs includes an end spaced from the back span, the end of each of the first and second legs being bent to secure the first and second legs within the central bore.

19. The circular stapling device of claim 13, wherein the locking member includes a torsion spring pivotably supported on the knife carrier.

20. The circular stapling device of claim 19, wherein the torsion spring includes spaced legs and a back span extending between the spaced legs, each of the spaced legs including a loop.

21. The circular stapling device of claim 20, further including a pivot member supported on the outer surface of the knife carrier, the pivot member received within the loops of the first and second legs.

22. The circular stapling device of claim 20, wherein the back span extends across the longitudinal slot and the catch member extends into the longitudinal slot.

23. The circular stapling device of claim 12, wherein the circular stapling device includes a handle assembly.

24. The circular stapling device of claim 12, wherein the elongate body is adapted to be coupled to a robotic surgical system.

* * * * *